United States Patent [19]

Okada

[11] 4,085,742
[45] Apr. 25, 1978

[54] ENDOSCOPE EQUIPPED WITH A FILM CASSETTE

[76] Inventor: Takeshi Okada, 13-45,, Terada-machi, Hachioji-shi Tokyo, Japan

[21] Appl. No.: 708,032

[22] Filed: Jul. 23, 1976

[30] Foreign Application Priority Data

Jul. 28, 1975 Japan .................................. 50-91656

[51] Int. Cl.² .............................................. A61B 1/00
[52] U.S. Cl. ............................................ 128/4; 128/6
[58] Field of Search ........................................ 128/3–8, 128/4, 6; 354/62, 63, 179; 242/71

[56] References Cited

U.S. PATENT DOCUMENTS

| 2,987,960 | 5/1961 | Sheldon | 128/6 |
| 3,608,547 | 9/1971 | Sato et al. | 128/6 |
| 3,730,175 | 5/1973 | Fukami et al. | 128/6 |
| 3,903,877 | 9/1975 | Terada | 128/6 |

Primary Examiner—Dalton L. Truluck
Assistant Examiner—Henry S. Layton

[57] ABSTRACT

An endoscope has a film cassette incorporated at the forward section of a sheath and a film cassette access opening is provided in the outer periphery of the forward section of the sheath. An outer cover means is detachably fitted over the outer peripheral portion of the forward section of the sheath and includes a hood member for protecting the front end surface of the forward section of the sheath and imparting no injury to the inner cavity of a human being which might otherwise occur by the edge of the forward end of the sheath.

3 Claims, 3 Drawing Figures

ENDOSCOPE EQUIPPED WITH A FILM CASSETTE

BACKGROUND OF THE INVENTION

This invention relates to an endoscope having a cassette removably incorporated in the forward section of an elongated sheath adapted to be inserted into the body cavity of a human being and having a film for photographing a desired portion of the body cavity of the human being.

A variety of endoscopes equipped with a cassette, a cartridge or a patrone (hereinafter referred to merely as a film cassette) are known in the art. Generally, the film cassette is incorporated in the forward section of a sheath of an endoscope by removing a metallic cap member threadably engaged with the front end portion of the sheath. With the cassette so incorporated an exposure window provided in a frame or housing of the cassette optically corresponds to a photographing window provided in the outer periphery of the forward section of the sheath. This type is called a side view type endoscope.

With the side view type endoscope equipped with a cassette, when the cassette is removed after film exposure from the forward section of the sheath, a cap member should be removed from the forward section of the sheath together with a cylindrical frame body having, for example, an observation window and illumination window which are optically coupled to an image guide fiber bundle and light guide fiber bundle in the longitudinal passage of the sheath. In the endoscope of this type parts of optical systems for photographing, observation and illumination and their supporting portions are exposed directly to an outer atmosphere, there being a fear that these parts or portions will be contaminated due to the deposition of dirt and dust etc. Since the frame body must be removed from the forward section of the sheath upon each removal of the cassette, the engaging portions of the parts are much worn, making it difficult to maintain liquidtightness and creating a clearance through which daylight is penetrated into a cassette receiving chanmber. As a result, there is a fear that a film will be unwarrantedly exposed by a daylight, that is, fogging will occur. Furthermore, a cumbersome operation is necessary in detachably incorporating the cassette into the forward section of the sheath.

SUMMARY OF THE INVENTION

It is accordingly an object of this invention to provide a functionally excellent endoscope equipped with a film cassette which is easy in detachable insertion into the forward section of a sheath without exerting any adverse effect over various optical systems.

In a film cassette equipped endscope according to a preferred embodiment of this invention a film cassette is inserted into, and removed from, a cassette receiving chamber in the forward section of a sheath through a film cassette access opening provided in the outer periphery of the forward section of the sheath. The endoscope according to this invention is of a front view type, that is, a photographing window together with an observation window and illumination window is provided at the front end surface of the forward section of the sheath. An outer cover means is detachably fitted over the outer peripheral portion of the forward section of the sheath and integrally equipped with a hood member for protecting the front surface of the forward section of the sheath against any excessive deposition of a foreign substance onto the front end surface of the forward section of the sheath and imparting no injury to the inner cavity of the human being which might otherwise occur by the edge of the forward end of the sheath. Upon fitting the outer cover means over the outer peripheral portion of the forward section of the sheath the cassette access opening is closed in a liquid-light fashion and, when the outer cover means is removed, the cassette access opening is opened to permit the built-in cassette to be removed. According to this invention, therefore, when the hood member equipped outer cover means is removed from the forward section of the sheath, the cassette can be readily taken out of the cassette receiving chamber. Even if the outer cover means is detached from the forward section of the sheath, parts of optical systems and their supporting portions are not exposed and in consequence no adverse effect is exerted over these parts or portions.

DESCRIPTION OF THE PREFERRED EMBODIMENT

Figure 1:
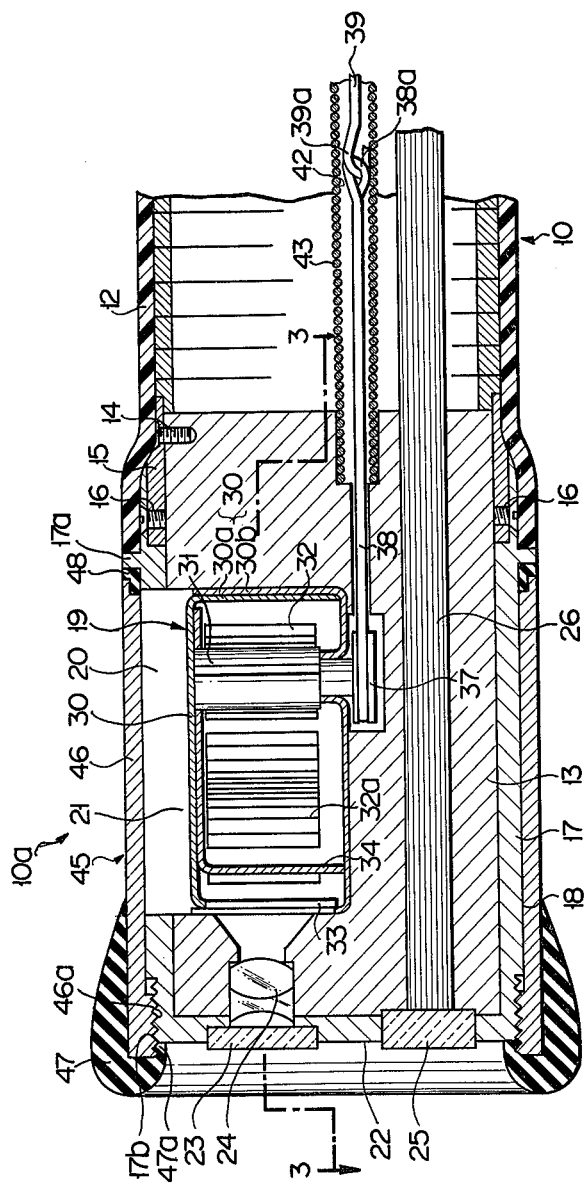
FIG. 1 is a longitudinal cross-sectional view showing a film cassette equipped endoscope according to a preferred embodiment of this invention with a forward section of a sheath exaggerated for detail representation.

Referring to the drawings, a film cassette equipped endoscope according to this invention includes a substantially elongated flexible sheath 10 adapted to be inserted into the body cavity (not shown) of a human being, and a control section 11 connected to the base end of the flexible sheath 10. The flexible sheath 10 has an outer flexible plastic tube 12 covered over the whole length thereof except for a forward section 10a. The forward section 10a of the sheath 10 includes a metallic block 13 constituting a body frame, a ring-like member 15 fixed by a set screw 14 on the outer surface of the metallic block 13, and a cylindrical casing 17 disposed on the outer surface of the block 13 so as to cover the outer periphery and forward end of the block 13 and fixed by set screws 16 on the ring-like member 15. In the neighbourhood of the rear end (to the right in FIG. 1) of the casing 17 an annular rib 17a is integrally formed on the outer periphery 18 of the casing 17, and the front end surface of a flexible outer tube 12 abuts against the annular rib 17a. A thread 17b is formed on the outer periphery 18 of the forward end portion (to the left in FIG. 1) of the casing 17. A rectangular access opening 20 for a film cassette 19 is formed on the outer periphery 18 of the forward section 10a of the flexible sheath 10. A substantially rectangular-shaped, cassette receiving chamber 21 is formed in that portion of the block 13 which communicates with the access opening 20 and the chamber 21 corresponds in shape to the outer configuration of the cassette 19. A photographing window 23 is disposed in a front end surface 22 of the forward section 10a of the flexible sheath 10, that is, the front portion of the casing 17. The window 23 leads to the film receiving chamber 21 through an optical system including a lens 24 disposed immediately behind the window 23 and mounted in the block 13. An illumination window 25 as shown and an image view window, not shown, are disposed at the front portion of the casing 17. A light guide fiber bundle 26 is optically coupled at the front end to the illumination window 25 and at the base end to the control section 11 through the sheath 10. An image guide fiber bundle, not shown, is also optically coupled at the front end to the image view window and at the base end to the control section through the sheath 10. These bundles and associated windows may be conventional ones and further explanation is therefore omitted.

As will be evident from the above-mentioned explanation the endoscope shown is of a front view type and the image view window, illumination window 25 and photographing window 23 are provided in that front end surface 23 of the forward section 10a which is substantially vertical to the axis of the sheath 10. This invention can also be applied to an endoscope of oblique view type in which the front end surface 22 of a forward end section 10a is inclined, to a certain extent, with respect to the axis of the sheath.

The film cassette 19 includes a housing means 30 detachably assembled together, a film take-up shaft 31 rotatably mounted on the housing means 30 and a film 32 loaded within the housing means 30, and an exposure window 33 is formed in the front end of the housing means 30. A film guide plate 34 is disposed within the housing means 30 and the film 32 is delivered from a film roll body 32a through the exposure window 33, while guided along the film guide plate 34, to the film take-up shaft 31 where it is wound. Reference numerals 35 and 36 are light shielding filters and the film 32 is passed through the filters 35 and 36 between which it is exposed.

Figure 2:
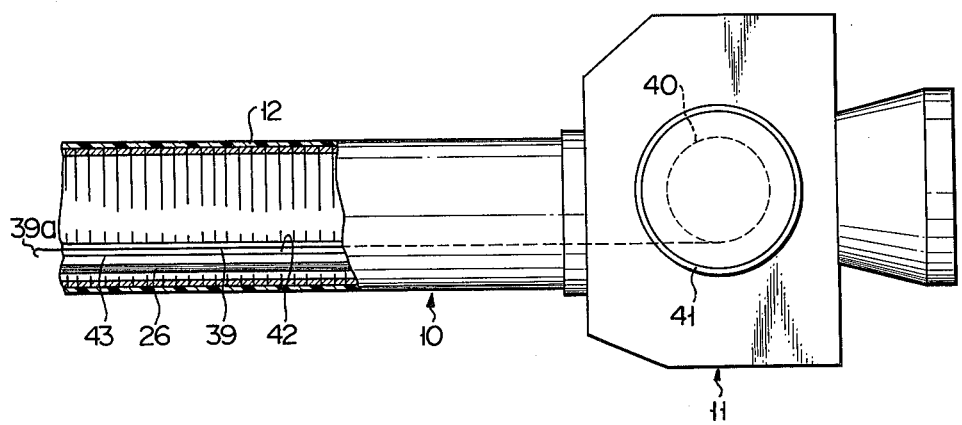
FIG. 2 is a side view, partly broken away, showing a control section and a base portion of the sheath connected to the control section.

One end of the take-up shaft 31 extends outwardly of the housing means 30 and a pulley 37 is fixed on the extending end of the take-up shaft 31. A string 38 is wounded at one end around the pulley 37 and a loop 38a is formed at a delivery end of the string 38. A hook 39a is formed at one end of an operating wire 39 and it is releasably anchored to the loop 38a of the string 38. As shown in FIG. 2 the base end portion of the wire 39 is wound around a take-up drum 40 located within the control section 11 and the take-up drum 40 is connected to an operating knob 41 placed outside of the control section 11. When the operating knob 41 is rotated by the operator in a counterclockwise diection in FIG. 2 so as to rotate the drum 40, the wire 39 is pulled outward. The string 38 and wire 39 are inserted in a longitudinal passage 42 in the sheath 10. As shown, the passage 42 is formed of a tightly helically wound small diameter wire tube 43, one end of which is supported in the block 13 and the other end of which is supported on the control section 11.

When the wire 39 is pulled by rotating the operating knob 41, the string 38 is drawn through a loop-hook connection to cause the pulley 37 to be rotated and the film 32 is wound frame by frame around the film takeup shaft 31. The film roll body 32a has no support shaft, but it may have a support shaft around which the film is wound.

Figure 3:
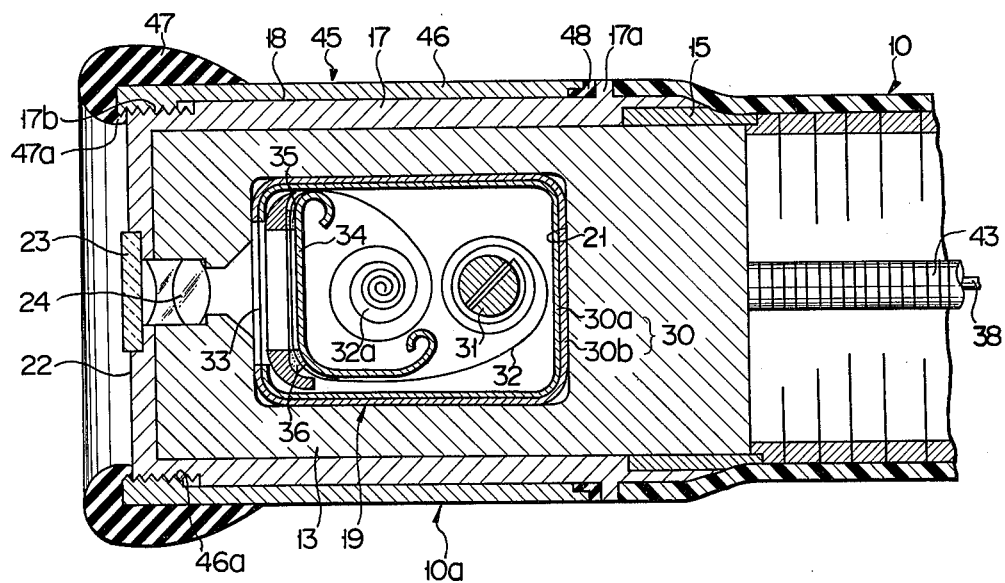
FIG. 3 is a cross-sectional view, as taken along line 3—3 in FIG. 1.

An outer cover means 45 is releasably mounted fitted over the outer periphery of the casing 17. The outer cover means 45 comprises a cylindrical, metallic hollow member 46 opened at both the ends and corresponding to the outer periphery of the forward section 10a of the sheath 10, and a hood member 47 formed by an elastic material, such as a rubber, which is integrally secured at the forward end portion (to the left in FIGS. 1 and 3) of the metallic hollow member 46. In the inner surface of the forward end portion of the hollow member 46 is formed an internal thread 46a which is engaged with the thread 17b of the casing 17. When the outer cover means 45 is fitted over the forward section 10a of the sheath 10 (that is, over the casing 17) with the thread 46a engaged with the thread 17b, the access opening 20 is completely closed. Since in this state the stepped rear end (to the right in FIG. 1 and 3) of the hollow member 46 abuts against a ring-like sealing member 48 which in turn is fitted into abutting engagement with the annular rib 17a of the casing 17, the access opening 20 is closed in a liquid-tight fashion. At the forward end of the outer cover means 45 the thread 46a of the hollow member 46 is engaged with the thread 17a of the casing 17 to obtain a liquid-tight seal. Furthermore, more positive liquid-tight seal is attained, since a portion 47a of the hood member 47 is abutted in a liquid-tight fashion against the front end surface 22. The hood member 47 per se is already employed in a known endoscope and it performs the double function of smoothly inserting the sheath 10 due to its smooth outer surface into the body cavity of a human being without injury to the inner surface of the body cavity and preventing a foreign substance from being excessively deposited onto the front end surface 22 of the forward section 10a, that is, onto the windows 23 and 25 in the front end surface 22 of the forward section 10a. Such a hood member is formed integral with a frame body on the forward section of the conventional endoscope. According to this invention the hood member 47 has integrally secured thereto the outer periphery of the forward end portion and front end portion of the hollow member 46 adapted to close the access opening 20 and constitutes the outer cover means 45 together with the hollow member 46. The hood member 47 can be bonded by a suitable adhesive to the hollow member 46 or be fused to the hollow member 46 during the molding of the hollow member. When the thread 46a of the hollow member 46 is disengaged from the thread 17b of the casing 17, the outer cover means 45 is readily separated, together with the hood member 47, from the forward section 10a of the sheath 10 to permit the access opening 20 to be opened. By so doing, the film cassette 19 incorporated in a position shown in FIG. 1 can be removed from the cassette receiving chamber 21 laterally of the forward section 10a of the sheath 10. Upon removal of the cassette 19 from the chamber 21 the string 38 and wire 39 are also drawn out. The wire 39 is drawn out enough for the operator to disengage the hook 39a of the wire 39 from the loop 38a of the string 38. By disassembling the side housings 30a and 30b the exposed film 32 can be taken out of the housing means 30.

Although in this embodiment the pulley 37 is fixed to the film take-up shaft 31, the pulley is so supported on the frame body in the forward section 10a of the sheath 10 that only when the cassette is incorpored in the cassette receiving chamber 21 the film take-up shaft 31 and pulley 37 can be rotated as a unit. In such arrangement, only the cassette can be removed from the housing means 30 with the pulley 37, string 38 and wire 39 left in the sheath 10.

As will be understood from the embodiment of this invention, when the outer cover means 45 integrally equipped with the hood member 47 is removed from the forward section 10a of the sheath 10, the film cassette 19 can be readily inserted into, and removed from, the forward section 10a of the sheath 10. Since in this case the various parts of the optical system and their support portions in the forward section 10a of the sheath 10 are not exposed, no adverse effect such as the deposition of dirt and dust, contamination etc. is exerted over these parts or portions. The outer cover means 45 performs the various functions of permitting the opening and closing of the access opening 20 in the outer periphery of the opening section 10a of the sheath 10, protecting the front end surface 22 of the section 10a of the sheath 10 by its hood member 47, and imparting no injury to the body cavity of the human being by its hood member which might otherwise occur by the edge of the front end of the sheath.

What is claimed is:

1. An endoscope equipped with a film cassette comprising:
    a sheath with a detachable film cassette incorporated in the forward end thereof;
    a control section connected to the base end of the sheath;
    a film cassette access opening formed in the outer periphery of the forward section of the sheath;
    outer cover means comprising a hollow member having a shape corresponding to that of the outer periphery of the forward section of the sheath and detachably fitted thereon to permit the film cassette access opening to be closed;
    and a hood member made of an elastic material and integrally secured to at least the outer periphery of the forward end portion of the hollow member to protect the front end surface of the forward section of the sheath and to impart no injury to the inner cavity of a human being during the insertion of the sheath into said inner cavity.

2. An endoscope according to claim 1, in which said hollow member has a forward end portion threadably engaged with a frame body of the forward section of the sheath and a rear end abutted in a liquid-tight fashion against the frame body through a sealing member.

3. An endoscope according to claim 1, in which said hollow member is made of a metal and said hood member is made of a rubber.

* * * * *